United States Patent [19]

Ryan

[11] Patent Number: 5,066,287
[45] Date of Patent: Nov. 19, 1991

[54] SAFETY MULTIPLE SAMPLE REAR ADAPTER ASSEMBLY

[75] Inventor: Dana W. Ryan, Franklin, Tenn.

[73] Assignee: Ryan Medical, Inc., Brentwood, Tenn.

[21] Appl. No.: 520,239

[22] Filed: May 7, 1990

Related U.S. Application Data

[63] Continuation-in-part of Ser. No. 224,920, Jul. 27, 1988, Pat. No. 4,923,445.

[51] Int. Cl.$^5$ ............................................. A61M 5/00
[52] U.S. Cl. ..................................... 604/240; 128/763
[58] Field of Search ............... 604/240, 241, 242, 195, 604/187, 232; 128/763, 764, 765

[56] References Cited

U.S. PATENT DOCUMENTS

| | | | |
|---|---|---|---|
| 3,884,229 | 5/1975 | Raines et al. | 604/242 |
| 4,398,544 | 8/1983 | Nugent et al. | 128/763 |
| 4,418,703 | 12/1983 | Hoch et al. | 128/763 |
| 4,679,571 | 7/1987 | Frankel et al. | 128/765 |

*Primary Examiner*—John D. Yasko
*Attorney, Agent, or Firm*—David P. Gordon

[57] ABSTRACT

Safety multiple sample rear adapter assemblies utilizing one or two molded components are provided. The two component devices have a male connector and a rear blood tube holder each of which is provided with locking devices. In assembly, the male connector is either lockingly forced into the rear blood tube holder, or lockingly screwed into the rear blood tube holder such that the male connector locks permanently into place inside the rear blood tube holder and cannot be removed. After use of the safety multiple sample rear adapter assembly, the assembly can be disposed of without danger of needlesticks, as the rear needle is shielded by the rear blood tube holder. In the single component device, the rear blood tube holder is provided with a male luer on one end, a receiving cylinder on the other end for receiving a standard blood collection vacuum tube, and a dividing wall which acts as the closed end of the receiving cylinder and which supports a nose which extends into the receiving cylinder. The nose holds the rearwardly extending needle as well as providing a device over which a resilient self-sealing needle covering sleeve may be attached. Another aspect of the assembly is a pediatric adapter which is inserted into the rear blood tube holder and accommodates smaller diameter blood collection vacuum tubes.

11 Claims, 4 Drawing Sheets

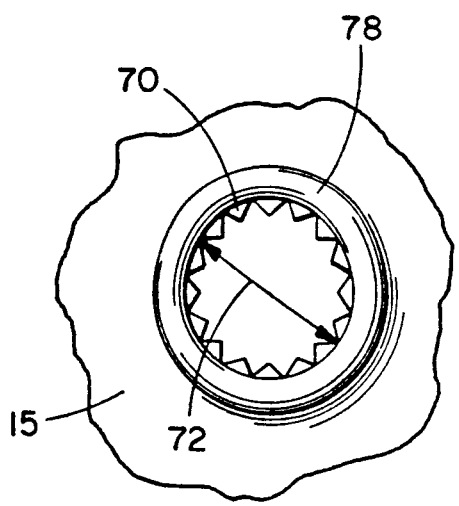
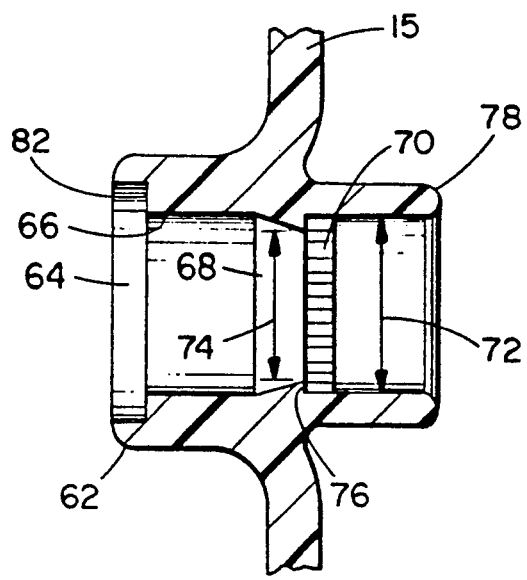
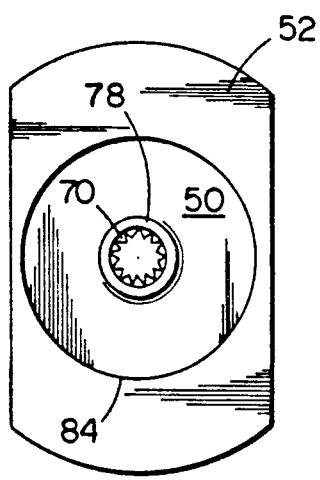
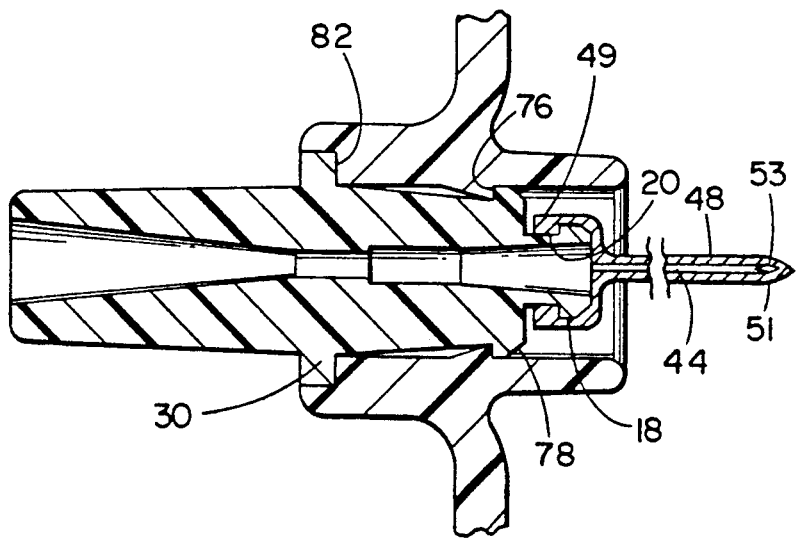
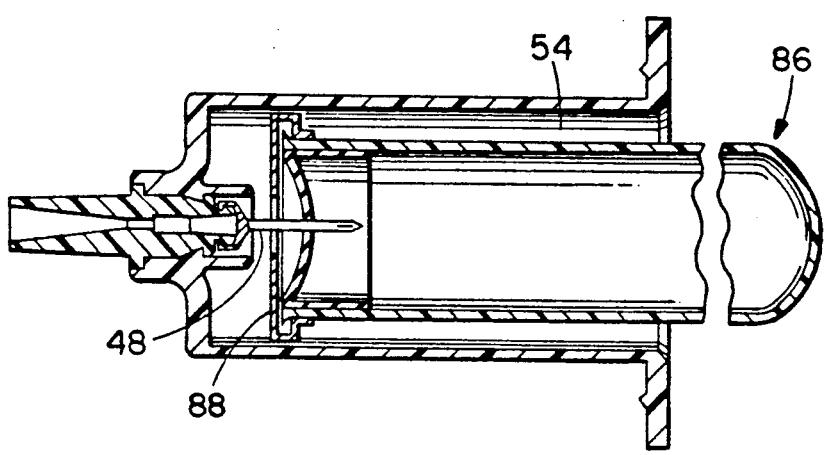

SAFETY MULTIPLE SAMPLE REAR ADAPTER ASSEMBLY

This Application is a continuation-in-part of copending Ser. No. 07/224,920 filed 7-27-88, now U.S. Pat. No. 4,923,445.

BACKGROUND OF THE INVENTION

This invention relates to medical devices for drawing blood samples, and more particularly to a safety multiple sample rear adapter assembly that makes it easier to draw blood samples from patients, and at the same time, provides substantial protection against needlesticks.

Drawing blood samples from patients is often a difficult task especially if a patient has small veins as is frequently the case with children, small women or the elderly. It is not unusual for a patient with small veins to be stuck more than once using standard blood collection needles before the needle is positioned properly in the vein to draw the blood sample. This problem can cause the patient physical distress and considerable anxiety. Under such conditions, the medical staff is also subjected to increased stress because of the patient's reaction to the difficulty of the procedure.

Winged needle devices, which give the phlebotomist greater control of the venipuncture procedure, can be helpful in solving the problem of taking blood samples from patients with small veins. The smaller winged needle device, because of its reduced size, allows the medical staff to position the needle more accurately, which significantly reduces the number of times a patient must be stuck with the needle to produce satisfactory blood sampling. However, standard winged needle devices do not have means for accepting blood collection vacuum tubes which provide negative pressure for drawing blood and in which the drawn blood is collected.

In order to permit the use of a winged needle device with a blood collection vacuum tube, it was proposed in U.S. Pat. No. 4,140,108 issued to Nugent to provide a blood collection assembly with a rear needle adapter for use in taking blood samples. The blood collection assembly of Nugent is comprised of several parts, including a rear needle adapter, and flexible tubing with hubs and needles on each end (one venipuncture needle and one rear needle for puncturing a stopper on a vacuum tube). The venipuncture needle is in open communication with the tubing and is held in the tubing by attachment to the hub. The rear needle is attached to the flexible tubing via the rear hub. The rear hub has external male helical threads which permit it to be screwed to and unscrewed from the forward hub portion of a standard rear blood tube holder which has reciprocating internal female helical threads. The standard rear blood tube holder also includes a receiving cylinder which is open at one end for receiving blood collection vacuum tubes.

In using the device disclosed by the Nugent patent, the rear needle attached to the male threaded hub is placed in the forward hub portion of a standard rear blood tube holder, and the rear hub on the flexible tubing is mated with the forward hub portion of a standard rear blood tube holder by screwing the two together The assembly is then ready to have standard blood collection vacuum tube(s) inserted in the receiving cylinder of the rear blood tube holder, such that the rear needle will puncture the stopper of the blood collection vacuum tube and blood will be collected. When the blood sampling procedure is finished, the venipuncture needle is removed from the patient's vein, and the rear needle is removed from the standard rear blood tube holder by unscrewing the hub holding the rear needle. The rear blood tube holder is then saved for subsequent uses. However, upon disassembly, the venipuncture and rear needles are contaminated and left completely exposed increasing the possibility of unwanted needlesticks occurring.

SUMMARY OF INVENTION

It is therefore an object of the invention to provide a safety multiple sample rear adapter blood collection assembly.

Another object is to provide a safety multiple sample rear adapter blood collection assembly, which can be used with a standard or safety winged needle venipuncture devices.

Yet another object is to provide a safety multiple sample rear adapter blood collection assembly which permanently locks a rear needle inside a rear blood tube holder, and which, when a filled blood collection vacuum tube is removed, shields the rear needle and significantly reduces the possibility of needlesticks.

Still another object is to provide a safety multiple sample rear adapter blood collection assembly with an insert to allow use of a reduced sized blood collection vacuum tubes for pediatric and other special uses.

According to a first aspect of the invention, the safety rear adapter assembly of the invention preferably comprises a male connector and a hollow rear blood tube holder. The male connector has hollow first and second ends and a hollow needle, the hollow first and second ends defining a throughbore that is connected with the needle. The first end of the male connector has a first locking means for locking with reciprocal means of the hollow rear blood tube holder. The second end of the male connector has a coupling such as a luer for coupling to a standard female luer adapter which is typically connected to a winged needle device. The hollow rear blood tube holder has an outer wall which forms a receiving cylinder with an open rear end for receiving blood collection vacuum tubes, and a front end having an opening for accepting the hollow front end of the male connector, the front end having locking means that mates to the male adapter. In assembling the safety rear adapter assembly the first and second locking means are designed so that, when mated together the result is a permanent connection.

Other preferred aspects of the invention relate to different locking means of the male connector and the rear blood tube holder. One locking configuration uses a ramp portion of increasing diameter and an increased diameter shoulder on the male connector and a ramp of decreasing diameter and a seat on the rear blood tube holder. The ramp and shoulder of the male connector are slid past the ramp at the front end of the rear blood tube holder such that the shoulder passes the ramp, rests in the seat, and cannot be removed from the rear blood tube holder because of the back face of the rear blood tube holder ramp. To prevent rotation of the male connector and the rear blood tube holder and further expedite mating, ratchet teeth may be added to both the ramp and shoulder of the male connector and to the seat of the rear blood tube holder. Axial motion of the male connector into the front end of the rear blood tube holder is restrained by a stop member that is located on the male connector or on the rear blood tube holder which restrains further motion of the male connector into the rear blood tube holder.

A second locking configuration uses a locking thread mechanism on the male connector and rear blood tube holder. The locking thread mechanism is chosen such that upon threading, permanent mating is accomplished.

Another embodiment of the invention has the safety multiple sample rear adapter molded from one piece of plastic, with a hollow receiving cylinder on one end for receiving a standard blood collection vacuum tube, a luer on the other end for coupling the safety multiple sample rear adapter to a mating luer, and a dividing wall between the receiving cylinder and the luer. A hollow needle with one sharp end is arranged to extend through the dividing wall with the sharp end of the needle in the receiving cylinder for puncturing a stopper on the blood collection vacuum tube. The dividing wall is arranged with a holder for holding a resilient self-sealing needle covering sleeve which extends over the sharp end of the needle. The one piece safety multiple sample rear adapter design eliminates the need for locking mechanisms altogether.

Each of the preferred embodiments of the safety multiple sample reap adapter is further provided with a pediatric adapter such that the diameter of the receiving cylinder may be adjusted to accommodate the smaller diameter of some blood collection vacuum tubes which are to be used.

Additional objects and advantages of the invention will become apparent to those skilled in the art upon reference to the detailed description in conjunction with the accompanying drawings.

BRIEF DESCRIPTION OF THE DRAWINGS

FIG. 3b is an end view of the front end of the rear blood tube holder of FIG. 1.

FIG. 3c is an end view of the rear end of the rear blood tube holder of FIG. 1 showing a flange.

FIG. 3d is an enlarged view of the cross section through the front end of the rear blood tube holder of FIG. 1.

FIG. 4 is an enlarged cross section showing the mating portions of the male connector and rear blood tube holder of FIG. 1.

FIG. 5 is a cross section showing a standard size blood collection vacuum tube in place in a rear safety multiple sample rear adapter assembly of FIG. 1.

FIGS. 7a-1 and 7a-2 are a cross section through and a front view of a male connector of a locking thread embodiment of the invention.

FIGS. 7b-1 and 7b-2 are partial cross section through and a partial front view of the rear blood tube holder of the locking thread embodiment of the invention.

DETAILED DESCRIPTION OF THE INVENTION

Figure 1:
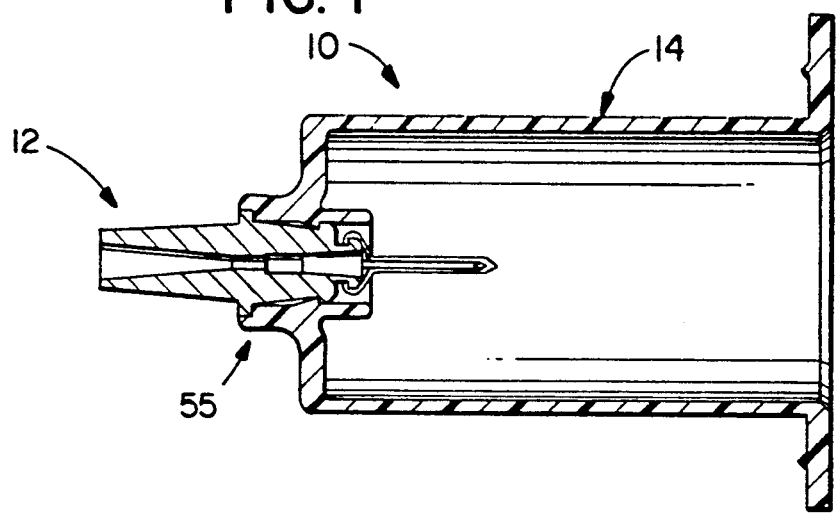
FIG. 1 is a cross section through a first embodiment of an assembled safety multiple sample rear adapter assembly of the invention having a male connector and a rear blood tube holder.
Figure 2A:
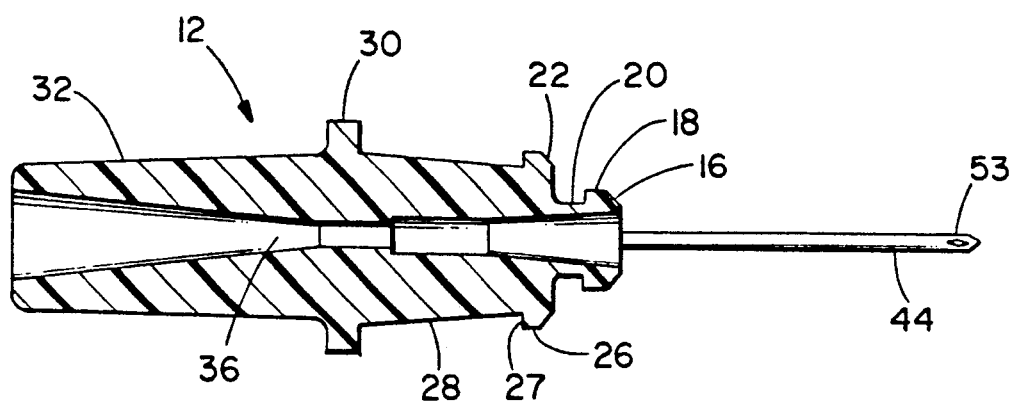
FIG. 2a is a cross section through the male connector of FIG. 1.
Figure 2B:
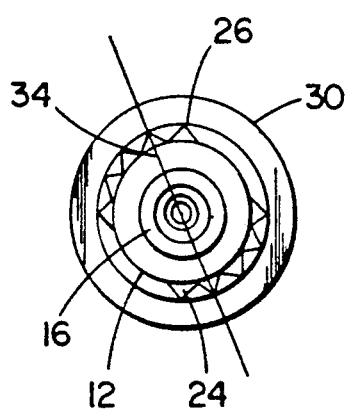
FIG. 2b is an end view of the first end of the male connector of FIG. 1.

As seen in FIG. 1, the safety multiple sample rear adapter assembly 10 of the invention comprises a male connector 12 and a rear blood tube holder 14. The male connector 12 as shown in FIG. 2a and FIG. 2b has a hollow front end with a nose 18 having a bevel 16 on the end of the nose, a groove 20 of reduced outer diameter relative to the outer diameter of the nose 18, a ratcheted ramp 22 which is of greater diameter than the diameter of the nose 18, which increases in diameter as it extends away from the nose, and which terminates in a ratcheted locking shoulder 26 of relatively constant diameter. A locking shoulder in turn terminates with a rear abutment surface 27. Rearward of the front end of the male connector 12 is a hollow middle portion with a stop member 30, and a generally cylindrical section 28 which lies between the abutment surface 27 of the ratcheted shoulder and the stop member 30. The generally cylindrical section 28 is provided with a reduced diameter relative to the shoulder 26. Rearward of the hollow middle portion is a rear end which comprises a standard male luer 32 as shown with an outer surface which tapers according to standard male luer specifications. As aforestated, the front end, middle portion, and rear end are hollow, and they together provide a continuous throughbore 36 of varying size. The portion of tapered bore 36 that begins at the nose 18 is arranged to permit a hollow needle 44 to be permanently attached therein, such as by gluing or bonding.

FIG. 4 shows the resilient self-sealing sleeve 48 covering the needle 44. The self-sealing sleeve 48 has an open end 49 which is arranged to fit over and grip the nose 18 while terminating in groove 20, and in this manner the self-sealing sleeve 48 is held in place. A closed end 51 of the self-sealing sleeve 48 extends slightly beyond the sharp end 53 of needle 44. As will be described in more detail hereinafter, self-sealing sleeve 48 permits multiple blood samples to be taken using the safety assembly by sealing off needle 44 between the taking of multiple blood samples.

Figure 3A:
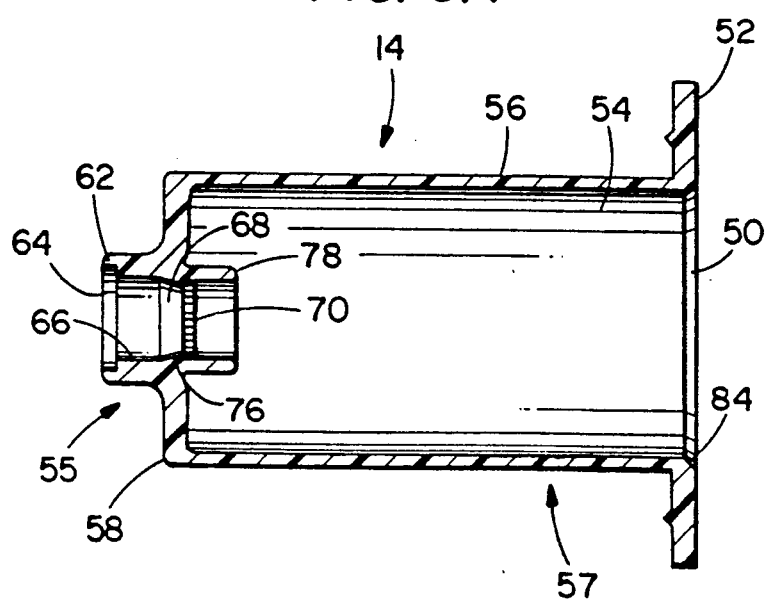
FIG. 3a is a cross section through the rear blood tube holder of FIG. 1.

Turning to FIGS. 3a–3d, the rear blood tube holder 14 is seen to have a front mating portion 55 and rear receiving cylindrical portion 57. The receiving cylindrical portion 57 has a circular opening 50 surrounded by a flange 52, and a chamber 54 formed by receiving cylinder wall 56. Receiving cylinder portion 57 terminates with a front end wall 58 which supports and is closed around front mating portion 55 which extends outward from the front wall 58. The front end of the front mating portion begins with a hollow cylinder 64 which has an inside diameter substantially equal to the diameter of the male connector stop member 30 shown in FIG. 2a, and with a depth substantially equal to the length of the stop member. Adjacent to hollow cylinder 64 is a reduced diameter cylinder 66 with an inside diameter substantially equal to the diameter of the male connector ratcheted shoulder 26 which is also substantially equal to the tooth apex diameter 34 shown in FIG. 2b. The reduced diameter cylinder 66 terminates in a ramp 68. Ramp 68 of the rear blood tube holder terminates at an annular ratchet 70, which has a root diameter 72 which is larger than the diameter 74 at the termination of the tapered bore 68 as shown in FIG. 3d. The difference in these two diameters forms a seat 76. The interior cylindrical wall 72 of collar 78 surrounds the annular ratchet and the collar extends beyond the annular ratchet protruding into the hollow middle portion 54 of the rear blood tube holder 14. The horizontal distance between seat 76 and seat 82 formed by the hollow cylinders 64 and 66 of the rear blood tube holder is substantially the same as the horizontal distance between the termination of the male connector ratcheted shoulder 27 and stop member 30 shown in FIG. 2a.

In connecting the male connector to the rear blood tube holder to make up the invention assembly as shown in FIG. 1 and FIG. 4, the male connector nose 18 is inserted in the rear blood tube holder front mating portion hollow cylinder 64. The nose 18 of the male connector is slid past the hollow cylinder 64 and into the reduced diameter cylinder 66 and then into ramp 68. At this point the male connector ratcheted ramp 22 is slid along rear blood tube holder ramp 68. The ratchet teeth of the male connector are flexible enough to permit them to deform to the contour of the rear blood tube holder ramp 68, which permits the male connector to be slid along rear blood tube holder ramp 68. When the male connector ratcheted ramp 22 reaches the beginning of the annular ratchet 70 it self-aligns and the male connector 12 self-rotates slightly so that the teeth of the male connector ratchet line up with the spaces between the teeth of the rear blood tube holder annular ratchet. In FIG. 2b the ratchet teeth 24 can be seen The male connector ratchet locking diameter (apex to apex diameter 34 seen in FIG. 2b), and the rear blood tube holder ratchet root diameter (valley to valley diameter 72 seen in FIG. 3b) are substantially the same as are the shape of the teeth which permits them to be interleaved. When the teeth are lined up the male connector ramp is slid forward so the teeth of the two ratchets do interleave. The male connector is slid as far into the rear blood tube holder as possible; the sliding distance being controlled by the male connector stop member 30 coming into contact with rear blood tube holder seat 82. The longitudinal movement of the male connector into the rear blood tube holder is sufficient to allow the male connector ratcheted ramp 22 to deform sufficiently to permit ratcheted shoulder 26 to slide past rear blood tube holder seat 76 as shown in FIG. 4. As ratcheted shoulder 26 clears seat 76 the deformed ratcheted ramp and shoulder return substantially to their original shape. If an attempt is made to pull the male connector out of the rear blood tube holder, the ratcheted shoulder 26 is restrained from being pulled out by rear tube holder seat 76 bearing on abutment surface 27. Since the male connector ratchet teeth are interleaved with the rear blood tube holder annular ratchet teeth no rotation of the male connector relative to the rear tube holder is possible. In this manner the male connector is permanently installed in the rear blood tube holder.

In use, the male connector is attached to the rear blood tube holder as described. A venipuncture needle which is part of a winged needle assembly (not shown) such as described in U.S. patent application Ser. No. 07/416,927 assigned to the assignee hereof, is placed in the vein of a patient. Blood flows from the vein of the patient through a flexible tube (not shown), through a female luer (not shown) attached to the flexible tube, through the male connector 12, and into the needle 44. Because the needle 44 is covered by sleeve 48, the blood can go no farther as the sleeve seals off the needle. At this point a blood collection vacuum tube 86 is pushed into the receiving chamber 54 with the rubber stopper 88 at the end of the collection tube pushing back the resilient self-sealing sleeve 48 and exposing the hollow needle 44 which penetrates the rubber stopper 88 all as shown by FIG. 5. The blood will then flow into the collection tube easily through the hollow needle aided by the presence of the vacuum in the collection tube 86.

When the vacuum blood collection tube is removed from receiving chamber 54, the resilient self-sealing sleeve 48 returns to its original shape covering and resealing the hollow needle so that it again appears as shown in FIG. 4, and so that blood does not continue to flow out of the needle 44. Another vacuum blood collection tube may then be introduced as aforedescribed to collect further blood samples. When all blood samples have been collected, the safety multiple sample rear adapter assembly 10 should not be reused. In disposal of the assembly, the needle 44 remains secure inside the receiving cylinder 54 of the rear blood tube holder 14 and is well shielded by resilient sleeve 48 and by cylindrical wall 56 to significant reduce the probability of accidental needlesticks. If the assembly is used with the preferred winged needle device of Ser. No. 07/416,927, then the venipuncture needle is withdrawn into the protective sheath of the winged needle device and no danger is presented from needlesticks from that source either.

Figure 6:
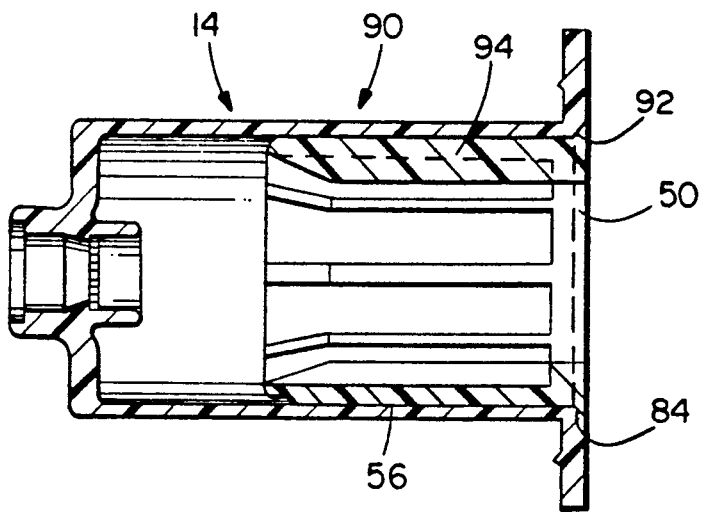
FIG. 6 is a cross section showing a pediatric adapter in place in the rear blood tube holder of FIG. 1.

If a smaller sample of blood is required as is the case in some pediatric and other situations, then a special reduced diameter blood collection vacuum tube adapter 90 (hereinafter referred to as a "pediatric adapter") is provided as shown in FIG. 6. The outside diameter of the pediatric adapter is substantially the same as the inside diameter of the receiving chamber walls 56. The inside "diameter" of the pediatric adapter 90 is formed by longitudinal ribs 94 that preferably run the length of the pediatric adapter. The pediatric adapter also includes a small beveled flange 92 at one end. The pediatric adapter 90 is installed in the rear blood tube holder 14 by pushing the pediatric adapter into the chamber 54 of the receiving cylinder until the beveled flange 92 of the pediatric adapter contacts the beveled edge 84 of the rear blood tube holder. A smaller diameter blood vacuum collection tube (not shown) may then be introduced into the pediatric adapter 90, with the ribs 94 of the pediatric adapter making contact with the tube which is guided and loosely supported thereby. The entire assembly then functions exactly as described above with relation to the standard blood collection vacuum tubes.

Figures 2, 7A:
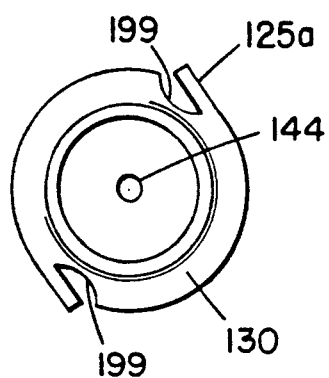
Figures 1, 7A:
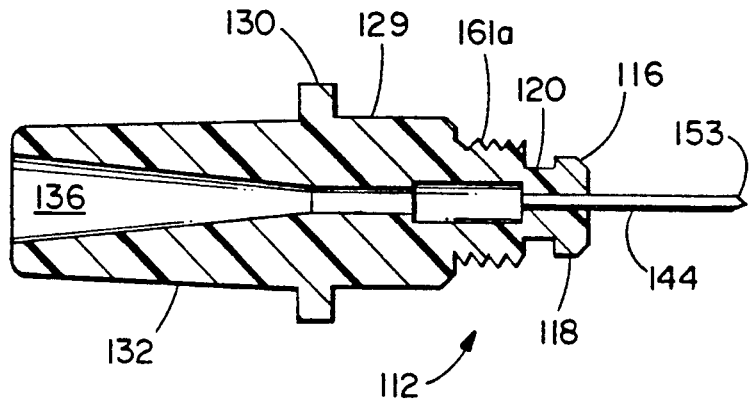

FIGS. 7a-1, 7a-2, 7b-1, 7b-2 and 7c illustrate an embodiment of the invention utilizing a locking thread system to permanently mate a male connector 112 to a rear blood tube holder 114. As seen in FIG. 7a, the male connector is hollow and substantially cylindrical, and defines a male luer on one end 132. The other end of male connector has a nose with ramp 116, shoulder 118, and a groove 120 rearward of the shoulder 118. The middle portion (which may be considered an extension of the nose end) of male connector 112 has a helical type male thread 161a around a portion of its circumference followed by a section 129 of increased diameter which is followed by a tabbed stop section 130 of even greater diameter. Tabbed stop 130, as seen in FIG. 7a-2, preferably includes two tabs 125a which are used as locking means as is more completely described below. The tabs 125a extend beyond the outer diameter of the remainder of stop 130, but are provided with bending flexibility by undercuts 199 in the stop member 130.

Figures 2, 7B:
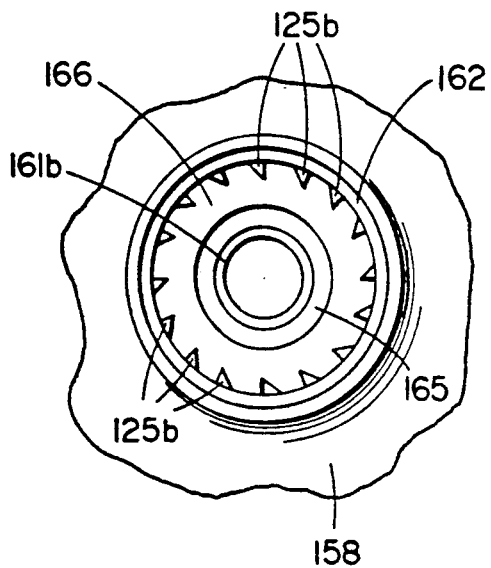
Figures 1, 7B:
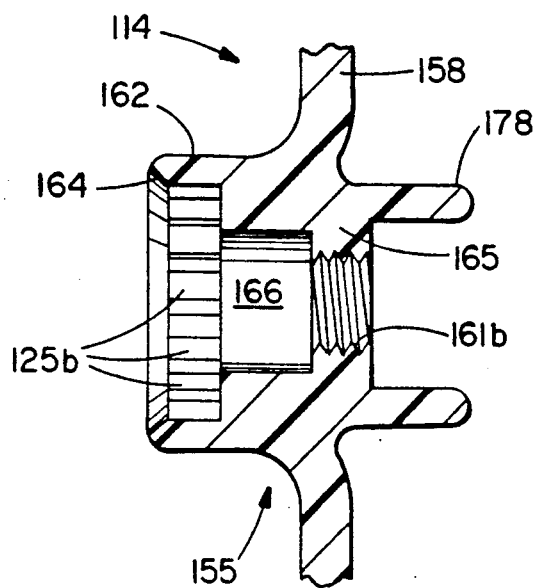

The rear blood tube holder 114 of the second embodiment shown in FIG. 7b has first and second ends. The first end (not shown) is substantially identical to the receiving cylinder of FIG. 1, and is of sufficient diameter to receive a standard blood collection vacuum tube. The first end terminates at a front end wall 158. Extending forward from the front end wall 158 is a front mating portion 155. The front end of the front mating portion 155 has a tapered hollow opening 164 which starts with an inside diameter slightly larger than the outside diameter of the tabbed stop member 130 of the male connector 112, and which terminates in a ratcheted seat 162 with ramped teeth 125b (seen in FIG. 7b-2). The ratcheted seat 162 in turn terminates in a reduced inner diameter cylinder 166 which terminates in wall 165 having a female threaded opening 161b. Extending rearward from wall 165 is a collar 178 which acts as a stop for blood collection vacuum tubes inserted into the rear blood tube holder 114.

Figure 7C:
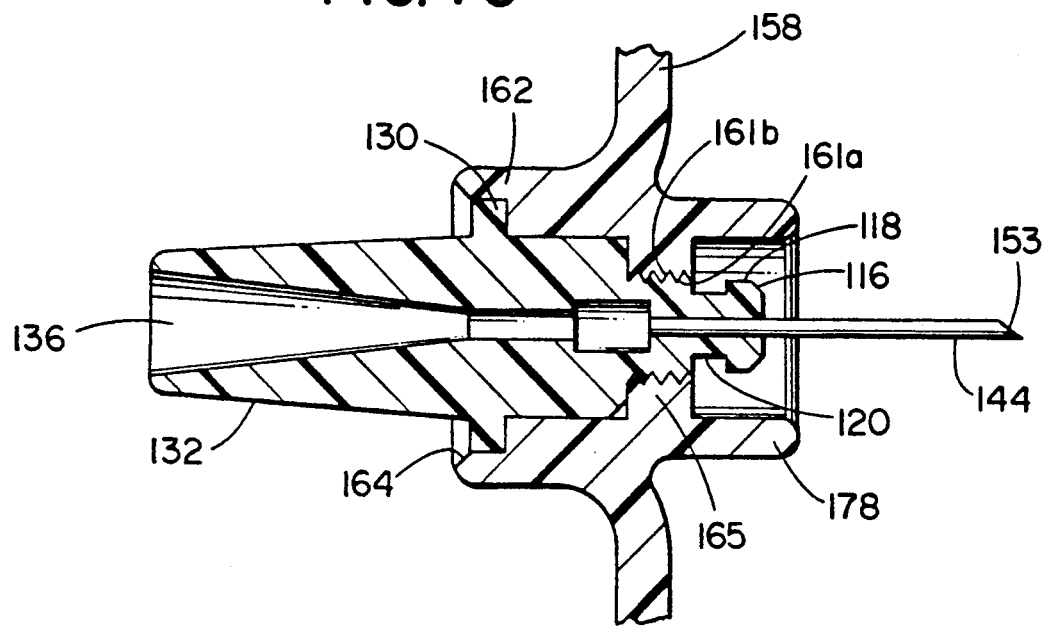
FIG. 7c is a partial cross section through the male connector and rear blood tube holder of FIGS. 7a-1 and 7b-1 illustrating how the male connector and rear blood tube holder mate by means of the locking thread system.

As will be appreciated by reference to FIG. 7c, the threaded opening 161b in wall 165 of the rear blood tube holder 114 is arranged with an inner diameter which matches the outer diameter of the male threaded middle portion of male connector 112. Similarly, ratcheted seat 162 and the ramped ratchet teeth 125b of the rear blood tube holder 114 are arranged with inner diameters which match that of the outer diameter of stop member 130 and tabs 125b respectively. Further, it will be appreciated that the outer diameter of the shoulder 118 of the nose of the male connector 112 is smaller than the inner diameter of threaded opening 161b in wall 165 of the rear blood tube holder 114, and that the axial distance between threaded opening 161b and seat 162 of the rear blood tube holder 114 is substantially equal to the axial distance between the thread 161a and the stop 130 of the middle portion of the male connector 112.

In mating the male connector 112 with the rear blood tube holder 114, the nose portion of the male connector 112 and needle 144 (as well as a self-sealing sleeve not shown) are inserted through the threaded hole 161b in wall 165 of the blood tube holder, until the male threaded section 161a of the male connector contacts wall 165 of the rear blood tube holder. Then, the male threaded section 161a is screwed into the female opening 161b until enlarged cylindrical portion 129 of the male connector contacts wall 165 of the rear blood tube holder. As the male connector and rear blood tube holder 114 are being screwed together, the tabbed stop 130 of the male connector 112 rotates in the ratcheted seat 162 of the rear blood tube holder, with the flexible tabs 125a flexing inwardly as they ride over ramped teeth 125b.

If rotational force is applied to the male connector in an attempt to remove the male connector 112 from the rear blood tube holder 114, the tabs 125a on the shoulder 130 of the of the male connector catch on the blunt portions of teeth 125b of seat 162 of the the blood tube holder 114 and deform. With tabs 125a deformed between the teeth 125b, the male connector 112 is locked into the rear blood tube holder 114 and cannot be removed by rotation. Also, if axial force is applied to the male connector in an attempt to remove the male connector 112 from the rear blood tube holder 114, the threads of threaded portion 161a of the male connector, and the threads of threaded opening 161b of the female connector act as stops, and prevent axial movement without rotation.

Figure 8:
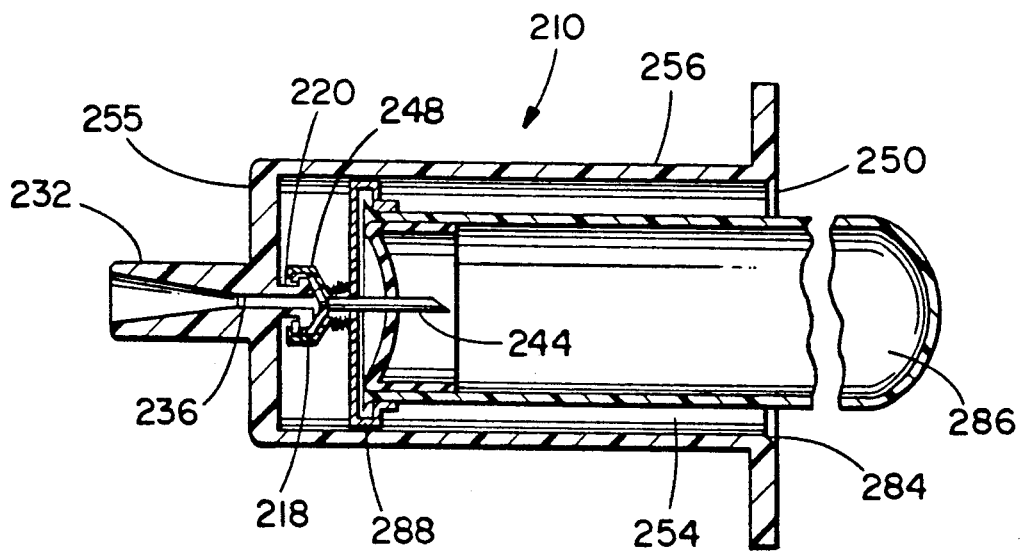
FIG. 8 is a cross section through a third embodiment of the invention which is a one piece molded safety multiple sample rear adapter.

Turning to FIG. 8, a safety multiple sample rear adapter assembly fabricated as a one piece molding is seen. The adapter 210 is comprised of a hollow receiving cylinder 256, a male luer 232 of substantially reduced outer diameter relative to the outer diameter of the cylinder 256, and a dividing wall 255 through which a throughbore 236 provides fluid communication between the receiving cylinder and male luer. The hollow receiving cylinder 256 has a circular open end 250 and a bevel 284 around the circular opening, and is of sufficient diameter to receive standard blood collection vacuum tubes 286 with front stoppers 288. The male luer 232 is sized and tapered according to standard luer specifications. The dividing wall 255 is effectively the front wall of the hollow receiving cylinder 256. Extending from the front wall 255 of the receiving cylinder 256 and back into the receiving cylinder 256 is a hollow rear extension which includes nose portion 218 and a groove 220 of reduced diameter relative to the nose portion 218. The hollow rear extension serves two purposes. First, it holds in place a needle 244 which is used to puncture the stoppers 288 of the 16 vacuum tubes 286. Second, it holds in place a resilient self-sealing needle covering sleeve 248 which as shown in FIG. 8 is punctured by the needle 244 and collapsed by the stopper 288 when the needle 244 punctures the stopper 288, but which as shown in FIG. 4 covers the sharp end of the needle 244 and stops blood flow after the vacuum tube is pulled off of the needle.

There have been described and illustrated herein safety multiple sample rear adapter assemblies. While particular embodiments of the invention have been described, it is not intended that the invention be limited thereby, as it is intended that the invention be as broad in scope as the art will allow. Thus, it will be understood by those skilled in the art that means other than ratcheted ramps and shoulders, and particular threaded arrangements could be utilized to establish permanent connection between two pieces of the assembly. For example, permanent connection could be accomplished by welding or gluing the two plastic parts together. Or, if desired, connecting pieces with locking threads having different thread widths, thread root diameters or thread pitch could be utilized to establish permanent connection upon screwing the pieces together. Further, while the male connectors of the two piece embodiments were described as having a male luer on one end, it will be appreciated that a male luer-lock could be utilized in lieu of the male luer. In fact, even a female luer or other connection means such as means which could connect directly to tubing could be utilized if the winged needle device terminates with tubing or a reciprocating mating connection means. Also, it should be appreciated that while the male connectors of the two piece embodiments were described as having a hollow needle inserted and glued into the nose of the connector, the needle could be insert molded or even formed in the molding process from plastic. Therefore, it will be appreciated by those skilled in the art that yet other modifications could be made to the provided invention without deviating from its spirit and scope as so claimed.

I claim:

1. A safety rear adapter assembly for coupling a fluid conduit means to a fluid collection means, said safety rear adapter assembly comprising:

a) a male connector having hollow first and second end portions and a hollow needle, said hollow first and second end portions defining a throughbore in fluid communication with said hollow needle, said first end portion having on its outer surface a first locking means, and said second end portion having coupling means for coupling to the fluid conduit means, and said outer surface of said first end portion of said male connector comprising a first ramp of increasing diameter as it extends from said first end portion toward said second end portion, and a shoulder of relatively constant outer diameter, said first ramp terminating in a first end of said shoulder, said shoulder having a second end terminating in portion of reduced diameter relative thereto; and b) a hollow rear blood tube holder with an outer wall defining a receiving cylinder with an open rear end for receiving the fluid collection means, and a front end having an opening therein for accepting at least a portion of said hollow first end portion of said male connector, said front end of said hollow rear blood tube holder having on its inner surface a second locking means, said inner surface of said front end of said hollow rear blood tube holder comprising a second ramp of decreasing inner diameter as it extends from said front end to said open rear end, said second ramp terminating in a chamber of inner diameter at least as large as said outer diameter of said shoulder, and said shoulder being of larger outer diameter than the inner diameter of said second ramp termination such that said termination of said second ramp and said shoulder form abutting locking surfaces, wherein in assembling said safety rear adapter assembly said first and second locking means are brought into permanent locking engagement.

2. A safety rear adapter assembly according to claim 1, wherein:
said first ramp and said shoulder of said male connector are ratcheted with a plurality of teeth, and said chamber of said rear blood tube holder has a ratcheted front end section with a plurality of grooves to mate with said plurality of teeth, thereby preventing rotation of said male connector relative to said rear blood tube holder.

3. A safety rear adapter assembly according to claim 1, wherein:
said male connector further includes a hollow middle portion between said hollow first and second end portions, said hollow middle portion having an outwardly extending stop member, said outwardly extending stop member having an outer perimeter of larger radial distance than said opening in said front end of said rear blood tube holder,
the axial distance between said stop member and said second end of said shoulder along a longitudinal axis of said male connector being substantially equal to the axial distance between said opening and said increased diameter chamber of said rear blood tube holder.

4. A safety rear adapter assembly according to claim 2, wherein:
said male connector further includes a hollow middle portion between said hollow first and second end portions, said hollow middle portion having an outwardly extending stop member, said outwardly extending stop member having an outer perimeter of larger radial distance than said opening in said front end of said rear blood tube holder,
the axial distance between said stop member and said second end of said shoulder along a longitudinal axis of said male connector being substantially equal to the axial distance between said opening and said increased diameter chamber of said rear blood tube holder.

5. A safety rear adapter assembly according to claim 1, wherein:
said hollow first end portion of said male connector includes a nose portion and a groove forward of said first ramp, said groove being between said nose portion and said first ramp and of an outer diameter smaller than said nose portion, and said nose portion being of outer diameter smaller than said outer diameter of said ramp.

6. A safety rear adapter assembly according to claim 5, further comprising:
c) a resilient self-sealing sleeve, said resilient self-sealing sleeve being closed at a first end and open at a second end and of a length and diameter such that said first end fits over a sharp end of said hollow needle, and said second end fits over said nose and engages said groove of said first end of said male connector.

7. A safety rear adapter assembly according to claim 4, wherein:
said hollow first end portion of said male connector includes a nose portion and a groove forward of said first ramp, said groove being between said nose portion and said first ramp and of an outer diameter smaller than said nose portion, and said nose portion being of outer diameter smaller than said outer diameter of said ramp, said safety rear adapter assembly further comprising
c) a resilient self-sealing sleeve, said resilient self-sealing sleeve being closed at a first end and open at a second end and of a length and diameter such that said first end fits over a said nose and engages said groove of said first end of said male connector.

8. A safety rear adapter assembly according to claim 1, wherein:
said coupling means of said second portion of said male connector comprises a male luer.

9. A safety rear adapter assembly according to claim 7, wherein:
said coupling means of said second portion of said male connector comprises a male luer.

10. A safety rear adapter assembly according to claim 1, where said fluid collection means is a pediatric blood collection vacuum tube, further comprising:
c) a cylindrical pediatric adapter having open first and second ends, an outer surface having a diameter substantially equal to the inside diameter of the said rear blood tube holder, and an inner surface having a diameter substantially equal to the outside diameter of the pediatric blood collection vacuum tube.

11. A safety rear adapter assembly according to claim 7, where said fluid collection means is a pediatric blood collection vacuum tube, further comprising:
c) a cylindrical pediatric adapter having open first and second ends, an outer surface having a diameter substantially equal to the inside diameter of the said rear blood tube holder, and an inner surface having a diameter substantially equal to the outside diameter of the pediatric blood collection vacuum tube.

* * * * *